United States Patent [19]

Di Battista et al.

[11] 4,293,466

[45] Oct. 6, 1981

[54] PIPERIDINE PHOSPHITE STABILIZERS FOR POLYMERS AND POLYMERS STABILIZED THEREBY

[75] Inventors: Piero Di Battista, San Donato Milanese; Renzo Fontanelli, Milan; Francesco Gratani, Sesto San Giovanni; Giuseppe Nelli, Milan, all of Italy

[73] Assignee: Montedison S.p.A., Milan, Italy

[21] Appl. No.: 966,562

[22] Filed: Dec. 5, 1978

[30] Foreign Application Priority Data

Dec. 2, 1977 [IT] Italy .............................. 30331 A/77

[51] Int. Cl.³ ...................... C07D 401/12; C08K 5/34
[52] U.S. Cl. ............................ 260/45.8 N; 260/23 H; 260/23 XA; 260/45.7 PH; 260/45.75 N; 260/45.8 NT; 260/45.85 S; 260/45.9 NC; 260/45.95 D; 260/45.95 E; 260/45.95 F; 260/45.95 R; 546/23; 546/186
[58] Field of Search ............... 260/45.8 NE, 45.8 NP, 260/23 H, 45.75 N; 546/16, 22

[56] References Cited

U.S. PATENT DOCUMENTS

| | | | |
|---|---|---|---|
| 2,753,368 | 7/1956 | Watson et al. ..................... 260/961 |
| 3,086,022 | 4/1963 | Meltzer et al. ..................... 546/188 |
| 3,759,926 | 9/1973 | Chalmers et al. ........... 260/45.8 NP |
| 4,088,629 | 5/1978 | Uhrhan et al. ............. 260/45.8 NP |
| 4,096,114 | 6/1978 | Minagawa et al. ......... 260/45.8 NZ |
| 4,104,248 | 8/1978 | Cantatore .................... 260/45.8 NP |
| 4,104,248 | 8/1978 | Cantatore ....................... 260/45.8 N |
| 4,144,224 | 3/1979 | Moser ......................... 260/45.8 NP |

*Primary Examiner*—Howard E. Schain
*Assistant Examiner*—R. A. White

[57] ABSTRACT

New derivatives of N,N'-4-piperidyl-tetraalkyl-substituted alkylene diamines are disclosed. These new compounds are useful for stabilizing thermoplastic polymers, in particular polyolefins, against sunlight, heat and oxidation. A process for producing the new compounds is also disclosed, as well as the use thereof as stabilizers of polymers and polymeric compositions.

11 Claims, No Drawings

PIPERIDINE PHOSPHITE STABILIZERS FOR POLYMERS AND POLYMERS STABILIZED THEREBY

THE PRIOR ART

As is known, the synthetic polymers in general suffer a certain degradation of their chemical-physical properties when they are exposed to sunlight or to other sources of ultraviolet light and when subjected to the various heat treatments during processing thereof.

It is also known, and usual, to add stabilizing substances to the synthetic polymers in order to improve their stability to sunlight and heat. For this purpose use is generally made to small quantities of benzophenones, benzotriazoles, amino-phenols, triazole compounds, phosphites, thiophosphites, kelates of transition metals, organo-stannic compounds, carbamates and thiocarbamates, esters of alfa-cyanoacrylic acid, etc., these substances being used either alone or in suitable combinations with each other.

The compounds mentioned, especially when employed in suitable combinations with each other, stabilize the synthetic polymers to a practically acceptable extent, but do not completely solve the problem.

It is known, too, that certain derivatives of 2,2,6,6-tetra-alkyl-piperidine are excellent stabilizers to sunlight and heat. In particular, U.S. Pat. No. 3,904,581 describes polymeric compositions stabilized with derivatives of 4-amino-2,2,6,6-tetra-alkyl-piperidine having the general formula:

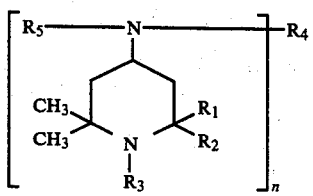

in which $R_2$ and $R_2$ may also be methyl, $R_3$ may also be an alkyl having 1 to 8 carbon atoms and, when n is 2, group $R_4$ may be, among other things, an alkylene having 2 to 6 carbon atoms and $R_5$ may be hydrogen.

Said piperidine derivatives considerably improve the photo- and thermo-stability of the synthetic polymers, but in order to reach satisfactory values it is necessary to use them in combination with other stabilizers. Furthermore, when they are used for thin articles, such as films and fibers, they are easily extracted during the washings or in general when brought into contact with water or with aqueous solutions of surfactants.

THE PRESENT INVENTION

An object of this invention is to provide a new class of stabilizers for thermoplastic synthetic polymers which are more effective than the prior art stabilizers in protecting said polymers against sunlight and heat, and more resistant to being removed when the polymers or polymeric compositions comprising them are brought into contact with aqueous media, as during washing.

This and other objects are achieved by this invention in accordance with which the thermoplastic synthetic polymers are stabilized by new derivatives of N,N'-piperidyl-tetralkylsubstituted alkylene diamines of the general formula:

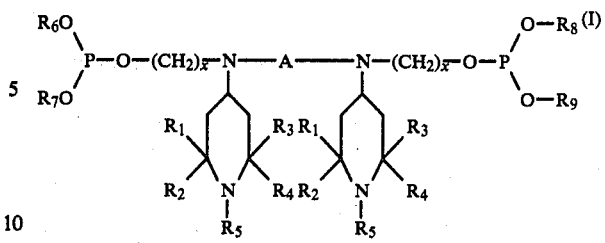

wherein: each of $R_1$, $R_2$, $R_3$ and $R_4$, which may be the same or different, may be an alkyl having 1 to 4 carbon atoms; $R_5$ may be a hydrogen atom or an alkyl having 1 to 4 carbon atoms; A is an alkylene group having 2 to 12 carbon atoms or a cycloalkylene group containing 3 to 12 carbon atoms; x is an integer from 1 to 10, and $R_6$, $R_7$, $R_8$ and $R_9$, which may be the same or different, are each a linear or branched alkyl group having 1 to 20 carbon atoms or a simple or substituted aryl group having 6 to 20 carbon atoms or $R_6$ and $R_7$ together and $R_8$ and $R_9$ together may form a linear or branched alkylene group having 2 to 20 carbon atoms, or a simple or substituted arylene group having 6 to 20 carbon atoms or a simple or substituted cycloalkylene group having 3 to 20 carbon atoms.

The presently preferred derivatives of the N,N'-4-piperidyl-tetralkyl-substituted alkylene diamines having general formula (I) for use in the practice of this invention are those in which $R_1$, $R_2$, $R_3$ and $R_4$ are methyl; $R_5$ is hydrogen; x is an integer from 2 to 6; each of $R_6$, $R_7$, $R_8$ and $R_9$ is an alkyl having 10 to 16 carbon atoms or $R_6$ and $R_7$ together and $R_8$ and $R_9$ together form an arylenegroup.

The term "synthetic thermoplastic polymers," as used in this specification and in the appended claims, includes:

polyolefins including the homopolymers of olefins such as low and high density polyethylene, polypropylene, polystyrene, polybutadiene, polyisoprene and the like, and copolymers of the olefins with other ethylenically unsaturated monomers such as ethylene-propylene copolymers, ethylene-butene copolymers, ethylene-vinylacetate copolymers, styrene-butadiene copolymers, styrene-acrylonitrile copolymers and acrylonitrile-styrene-butadiene copolymers;

polyvinyl chloride and polyvinylidene chloride, including both the homopolymers and the copolymers of vinyl chloride and of vinylidene chloride with each other or each with vinyl acetate or other ethylenically unsaturated monomers;

polyacetals such as polyoxymethylene and polyoxyethylene;

polyesters such as polyethylene terephthalate;

polyamides such as nylon 6, nylon 6-6 and nylon 6-10, and polyurethanes.

Such synthetic polymers can be employed either as powder or as granules, or as shaped articles, e.g. fibers, films, sheets and other shaped articles and also as latex and foams.

The presently preferred synthetic polymers for use in practice of this invention are the polyolefins deriving from monomers having the general formula:

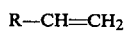

wherein R is an alkyl or aryl group, or a hydrogen atom.

The presently preferred polyolefin is polypropylene, consisting prevailingly of isotactic macromolecules and obtained by the polymerization of propylene in the presence of stereo-specific catalysts.

The amount of the derivative of N,N'-4-piperidyl-2,2,6,6-tetralkyl-substituted alkylene diamine having general formula (I) to be added to the synthetic polymer according to the present invention is such as to prevent degradation of the polymer. This amount is not critical and can vary in a wide range as a function of type, properties and particular uses of the synthetic polymer to be stabilized. Generally, said derivatives can be added to the polymer in amounts comprised between 0.01 and 5.0% by weight, based on the polymer weight; in practice, however, the effective amount varies as a function of the type of polymer to be stabilized. Thus, for instance, in the case of polyolefins, an effective amount can range from 0.01 to 2% by weight; in the case of polyvinyl chloride and of polyvinylidene chloride such amount can vary from 0.01 to 1% by weight, while in the case of polyurethanes and of polyamides the effective amount varies from 0.01 to 5% by weight.

The above-mentioned stabilizers can be employed either alone or in admixture with other known additives such as antioxidants, adsorbents of ultraviolet rays, pigments, fillers, basic nitrogen containing polycondensates, stabilizers, etc. Some examples of such additives are oxy-benzotriazoles, oxy-benzophenones, Ni-stabilizers, metal soaps, phenolic antioxidants, phosphites, thioesters, hydroquinone derivatives, triazine compounds, acryl-amino-phenols, benzyl-phosphonates, etc. Such additives may be employed along with the derivatives of alkylene-diamine having general formula (I) according to the present invention, at a ratio by weight ranging from 0.5:1 to 3:1.

The incorporation of the alkylene diamine derivative (I) or of the mixture containing said derivative with the synthetic polymer can be carried out according to different conventional procedures and at any stage prior to or during the manufacturing of the shaped articles from said polymer. Thus, for example, the additives in powder form can be simply mixed with the polymer under stirring; or the polymer can be mixed with a solution of the stabilizers in a suitable solvent, whereupon said solvent is evaporated; or the stabilizers can be added to the polymer at the conclusion of polymerization.

Furthermore the stabilizing effect can be achieved by applying the stabilizer to the manufactured article, for example by immersing the article in a solution or dispersion of the stabilizers and by successively evaporating the solvent or the dispersant.

The alkylene-diamine derivatives having the aboveindicated general formula (I) are characterized in that they possesses:
- a high degree of stabilizing activity, as compared with the known stabilizers, with respect to the synthetic thermoplastic polymers, towards the degradation caused by heat, sunlight and ageing;
- good consistency with the synthetic thermoplastic polymers without any appreciable degree of coloring;
- good consistency with the other known stabilizers or additives without coloring the polymer to be stabilized or reducing their stabilizing activity;
- low degree of thermal sublimation or exudation, and
- low degree of extraction during the treatment with water or with aqueous solutions.

The derivatives of N,N'-4-piperidyl-2,2,6,6-tetralkyl-substituted alkylene diamine having general formula (I) are preferably synthetized according to the following scheme:

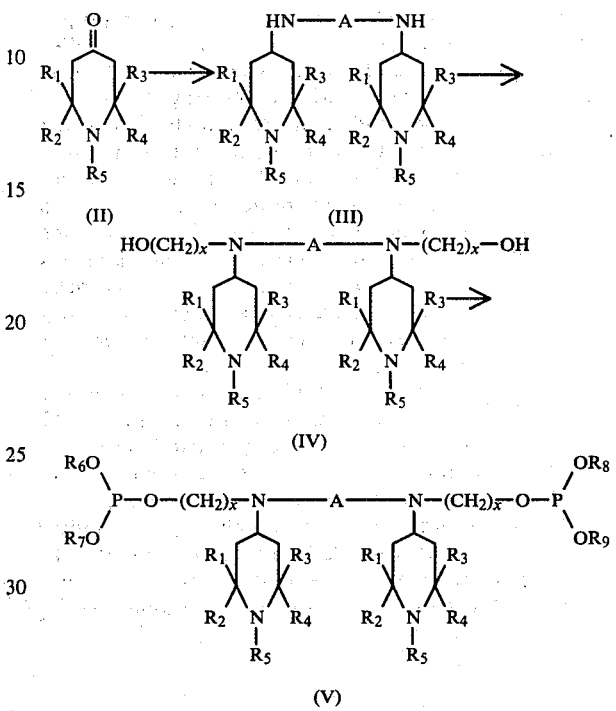

The reaction (II)→(III) can be carried out by reacting compound (II) with an alkylene diamine and hydrogen under pressure in the presence of a hydrogenation catalyst such as platinum.

The reaction (III)→(IV) can be conducted in an alcoholic solution by reacting the diamine (III) with a ω-halogenated alcohol in the presence of an agent capable of fixing the acid.

The reaction (IV)→(V) can be conducted by reacting the dialcohol (IV) with a di-alkyl-chloro phosphite.

The following non-limiting examples are given for a more detailed understanding of the present invention and for enabling the art to practice the same. Unless otherwise specified, all the parts in the examples are to be understood as parts by weight.

EXAMPLE 1

Preparation of bis-O,O-phenylene-O-[N,N'-diethyl-N,N'-(2,2,6,6-tetramethyl-4-piperidyl) 1,6-hexamethylene diamino]phosphite In a 500 cc flask equipped with a stirrer, a thermometer and a reflux cooler, 45 g (0.55 mole) of ethylene chlorohydrin dissolved in 50 cc of methanol were added to a solution of 100 g (0.25 mole) of N,N'-bis-(2,2,6,6-tetramethyl-4-piperidyl) 1,6-hexamethylene diamine dissolved in 120 cc of methanol.

The mixture was heated at reflux up to the boiling temperature and 22 g (0.55 mole) of NaOH in tablets were gradually added thereto in 8 hours. Following the addition of NaOH, the mass was heated at reflux for a further 2 hours, then cooled down and filtered to separate the sodium chloride that had formed. The filtrate was dried to evaporate the methanol, whereupon the residue was crystallized in dioxane. The resulting product had a melting point of 139°–141° C. and a content of N=11.6% (calculated value: 11.7%).

In a 500 cc flask, 48.2 g (0.1 mole) of the compound so obtained were dissolved in 250 cc of methylene chloride and the solution thus obtained was treated with a solution of 34.9 g (0.2 mole) of O.phenylene-chlorophosphite in 50 cc of methylene chloride, at a temperature ranging from 5° to 10° C. The mixture was stirred for 2 hours at room temperature, then it was cooled down to 0° C. and gaseous ammonia was blown thereinto for 4 hours.

The ammonium chloride that had formed was removed by filtration and the solvent was evaporated under vacuum.

The obtained product was in the form of powder and the elemental analysis gave the following results:

|   | Found values | Calculated values |
|---|---|---|
| C = | 67.74% | 63.3% |
| H = | 8.20% | 8.44% |
| P = | 8.00% | 8.18% |
| N = | 7.15% | 7.39% | corresponding to the compound:

$$\underset{O}{\overset{O}{\bigcirc}}\!\!P\!-\!O\!-\!(CH_2)_2\!-\!N\!-\!\!-\!(CH_2)_6\!-\!\!-\!N\!-\!(CH_2)_2\!-\!O\!-\!P\underset{O}{\overset{O}{\bigcirc}}$$

with 2,2,6,6-tetramethyl-4-piperidyl groups on the nitrogens.

Stabilization Tests 100 cc of chloroform containing, dissolved therein, bis O,O phenylen O-[N,N'-di-ethyl-N,N'-(2,2,6,6-tetramethyl-4-piperidyl) 1,6-hexamethylene diamino]-phosphite as prepared in Example 1 and in amounts as indicated in Table I, were added to 100 g of non-stabilized polypropylene (having an intrinsic viscosity, measured in tetralin at 130° C., of 162 cc/g, a residue after extraction of the crude polymerizate with n-heptane of 96.5%, and ashes=80 ppm).

Each mixture was stirred for about 6 hours at room temperature in a rotary evaporator and then dried at 0.01 mm Hg at 50° C. for 1 hours. The additioned powder so obtained was extruded in a Brabender extruder at 220° C. and granulated. The granules were molded to films at 200° C. for 3 minutes between two square steel plates measuring 20×20 cm, and under a load of 1000 kg.

The films so obtained exhibited a uniform thickness of 50–60μ and were practically colorless and homogeneous. On the films so prepared, the thermo-oxidative stability, at different temperatures and at 760 mm Hg of oxygen, and the photo-oxidative stability were determined. The thermo-oxidation induction period (Ip), intended as the time required to get a quick increase of the oxygen absorption rate was taken as thermo-oxidative stability value. The photo-oxidative stability test was carried out by exposing the films in an apparatus of the type Xenotest 450 manufactured by Messrs. Hanau and by determining on said films the concentration variations of the carbonyl groups by means of I.R. spectrometry and the variation of the mechanical properties by means of bending tests.

The induction period (Ip) necessary to bring about a rapid increase in the formation rate of the carbonyl groups was taken as photo-oxidative stability value, and the exposure time to the Xenotest, necessary to cause the rupture of the film by means of one bending only, as embrittling time.

To determine the thermo-oxidative stability, 0.2 g of each of the films obtained was cut to pieces and introduced into a cell of about 50 cm$^3$, wherein an oxygen atmosphere was created by repeatedly removing and introducing oxygen. The cell was connected with an oxygen measuring device equipped with a recorder of the volumes absorbed. The cell was immersed in a thermostatic bath maintained at a temperature of 170° C. The induction period (Ip) values measured on the films are recorded in Table I.

To determine the photo-oxidative degradation, some cut pieces of film were mounted on the proper supports of apparatus Xenotest 450 and exposed to the light of a xenon lamp 4500 W, filtered to have an emission spectrum as similar as possible to the solar spectrum. The temperature in the exposure chamber was kept at 50°±2° C. and the relative humidity at 35±5%. At intervals of time, film samples were taken in order to measure the I.R. absorption in proximity of the wave length of 1720 cm$^{-1}$, corresponding to the absorption of the carbonyl groups. With a view to evaluating the concentration of the carbonyl groups, a conventional value of the molar absorption coefficient equal to 300 l/mole x cm was assumed. The induction period (Ip) values measured on the films are recorded in Table I.

TABLE I

| Stabilizer % by weight | Thermo-oxidative stability | | Photo-oxidative stability | |
|---|---|---|---|---|
| | Ip in h. | Temp. °C. | Ip in H. | Embrittlement time in hours |
| — | 0 | 170 | 60 | 70 |
| 0.30 | 4 | 170 | 850 | 920 |
| 0.50 | 7 | 170 | 1400 | 1500 |

The thermo-oxidative stability tests recorded above were conducted also on the mixture consisting of polypropylene/bis O,O-phenylen-O-[N,N'-diethyl-N,N'-(2,2,6,6-tetramethyl-4-piperidyl) 1,6-hexamethylene diamino]phosphite in the same ratios indicated hereinbefore. The results obtained were wholly like those obtained from the film, which proved that the hot processing necessary to obtain the films did not sensibly alter the composition stability.

EXAMPLE 2

Preparation of bis-O,O-di-lauryl-O-[N,N'-di-ethyl-N,N'(2,2,6,6 tetramethyl-4-piperidyl) 1,6-hexamethylene diamino]phosphite.

In a 500 cc flask, 48.2 g (0.1 mole) of the reaction product between N,N'-bis-(2,2,6,6-tetramethyl-4-piperidyl) 1,6-hexamethylene diamine and ethylene chlorohydrin, prepared according to Example 1, were dissolved in 250 cc of methylene chloride and treated with a solution of 84.1 g (0.2 mole) of lauryl-chlorophosphite in 100 cc of methylene chloride. The mixture was stirred for 2 hours at room temperature, after which it was cooled to 0° C. while gaseous ammonia was blown in for 4 hours. The ammonium chloride so formed was separated by filtration and the solvent evaporated under vacuum. The resulting product was a powder having the following elemental analysis:

C=70.5%
N=4.5%
H=12.1%
P=4.7% in accordance with the centesimal calculated composition
C=71.14%
N=4.37%
H=12.17%
P=4.84% corresponding to the compound:

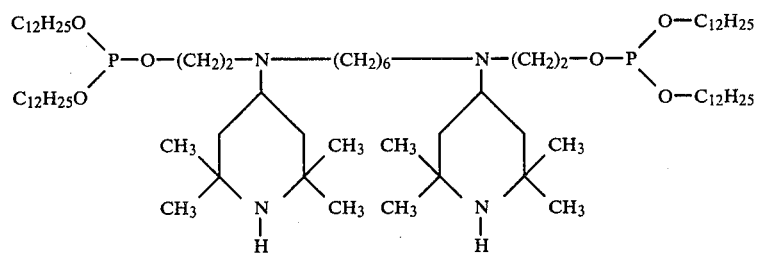

Stabilization Tests

By operating according to Example 1, films having a uniform thickness of 50–60μ were prepared. The samples were subjected to the thermo-oxidative and photo-oxidative stability tests of Example 1, the results obtained being recorded in Table II.

TABLE II

| Stabilizer % by weight | Thermo-oxidative stability | | Photo-oxidative stability | |
|---|---|---|---|---|
| | Ip in h. | Temp. °C. | Ip in h. | Embrittlement time in hours |
| — | 0 | 170 | 60 | 70 |
| 0.3 | 3.8 | 170 | 750 | 780 |
| 0.5 | 7.1 | 170 | 1500 | 1500 |

What we claim is:

1. Compositions comprising synthetic thermoplastic polymers stabilized to sunlight, to heat and to ageing, and having incorporated therein, in an amount sufficient to prevent degradation of the polymer, a compound having general formula:

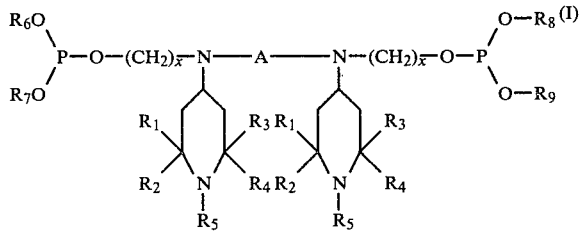

wherein: each of $R_1$, $R_2$, $R_3$ and $R_4$, which may be the same or different, may be an alkyl having 1 to 4 carbon atoms; $R_5$ may be a hydrogen atom or an alkyl having 1 to 4 carbon atoms; A is an alkylene group having 2 to 12 carbon atoms or a cycloalkylene group containing 3 to 12 carbon atoms; x is an integer from 1 to 10, and $R_6$, $R_7$, $R_8$ and $R_9$, which may be the same or different, are each a linear or branched alkyl group having 1 to 20 carbon atoms or a simple or substituted aryl group having 6 to 20 carbon atoms or $R_6$ and $R_7$ together and $R_8$ and $R_9$ together may form a linear or branched alkylene group having 2 to 20 carbon atoms, or a simple or substituted arylene group having 6 to 20 carbon atoms or a simple or substituted cycloalkylene group having 3 to 20 carbon atoms.

2. Compositions according to claim 1, in which, in formula (I), $R_1$, $R_2$, $R_3$ and $R_4$ are methyl; $R_5$ is hydrogen; x is an integer from 2 to 6; each of $R_6$, $R_7$, $R_8$ and $R_9$ is an alkyl having 10 to 16 carbon atoms or $R_6$ and $R_7$ together and $R_8$ and $R_9$ together form an arylene group.

3. Compositions according to claim 1, in which the compound of general formula (I) is present in an amount ranging from 0.01 to 5% by weight on the weight of the polymer.

4. Compositions according to claim 1, in which the polymer is a polyolefin.

5. Compositions according to claim 4, in which the compound of general formula (I) is present in an amount ranging from 0.01 to 2% by weight on the weight of the polyolefin.

6. Compositions according to claim 1, in which the polymer is polyvinyl chloride or polyvinylidene chloride.

7. Compositions according to claim 6, in which the compound of general formula (I) is contained in an amount ranging from 0.01 to 1% by weight on the weight of the polymer.

8. Compositions according to claim 1, in which the polymer is a polyurethane or a polyamide.

9. Compositions according to claim 8, in which the compound of general formula (I) is contained in an amount ranging from 0.01 to 5% by weight on the weight of the polymer.

10. Compositions according to claim 1, in which compound I is employed in admixture with at least one additive selected from the group consisting of oxy-benzotriazoles, oxy-benzophenones, Ni-stabilizers, metal soaps, phenolic antioxidants, phosphites, thioesters, hydroquinone derivatives, triazines, acyl-amino phenols, and benzyl phosphonates.

11. Compositions according to claim 10, in which the ratio of additive or additives to the compound of formula (I) is from 0.5:1 to 3:1.

* * * * *